United States Patent [19]

Koschke et al.

[11] Patent Number: 4,494,411

[45] Date of Patent: Jan. 22, 1985

[54] PRESSURE DETECTOR COMPRISING A CYLINDRICAL CAVITY RESONATOR HAVING A FRONT SURFACE MADE AS A DIAPHRAGM

[75] Inventors: Peter Koschke, Bad Feilnbach; Pavel Novak, Munich, both of Fed. Rep. of Germany

[73] Assignee: Fraunhofer-Gesellschaft zur Forderung der angewandten Forschung e.V., Fed. Rep. of Germany

[21] Appl. No.: 495,360

[22] PCT Filed: Aug. 27, 1982

[86] PCT No.: PCT/EP82/00183

§ 371 Date: Apr. 27, 1983

§ 102(e) Date: Apr. 27, 1983

[87] PCT Pub. No.: WO83/00925

PCT Pub. Date: Mar. 17, 1983

[30] Foreign Application Priority Data

Sep. 9, 1981 [DE] Fed. Rep. of Germany ....... 3126093

[51] Int. Cl.³ .......................... A61B 5/00; G01L 9/12
[52] U.S. Cl. ...................................... 73/724; 73/431; 73/756; 128/748; 128/903
[58] Field of Search ................. 73/724, 718, 756, 431; 128/748, 903

[56] References Cited

U.S. PATENT DOCUMENTS

| 3,962,921 | 6/1976 | Lips | 73/724 |
| 3,968,694 | 7/1976 | Clark | 73/724 |
| 4,016,764 | 4/1977 | Rice | 73/724 |
| 4,026,276 | 5/1977 | Chubbuck | 73/724 |
| 4,062,354 | 12/1977 | Taylor | 128/748 |
| 4,149,423 | 4/1979 | Frosch | 73/724 |
| 4,186,749 | 2/1980 | Fryer | 73/724 |
| 4,206,762 | 6/1980 | Cosman | 128/748 |
| 4,237,900 | 12/1980 | Schulman et al. | 128/903 |
| 4,265,252 | 5/1981 | Chubbuck | 128/748 |
| 4,378,809 | 4/1983 | Cosman | 128/748 |

FOREIGN PATENT DOCUMENTS 2262032 12/1972 Fed. Rep. of Germany .
2303465 12/1980 Fed. Rep. of Germany .

OTHER PUBLICATIONS

Funkschau 1961/Heft 10, Wendel–Topfkreise fur Kreisguten uber 300, Von Rudolf Dierke.

*Primary Examiner*—Donald O. Woodiel
*Attorney, Agent, or Firm*—Hayes, Davis & Soloway

[57] ABSTRACT

There has been described a pressure detector that comprises a cylindrical resonator cavity (21) with a front surface made as a diaphragm (23) and an oscillator (29). The frequency of the oscillator signal is a criterion for the pressure acting upon the diaphragm; the oscillator signal is wirelessly radiated (32) and can be processed with an adequate receiver with frequency meter or the like. The current is supplied via a built-in battery (31) or by wireless irradiation. For measuring the intracranial pressure, the pressure detector is implanted in the skull bone (11) by means of a special adapter sleeve (18).

12 Claims, 3 Drawing Figures

PRESSURE DETECTOR COMPRISING A CYLINDRICAL CAVITY RESONATOR HAVING A FRONT SURFACE MADE AS A DIAPHRAGM

The invention concerns itself with a pressure detector according to the preamble of claim 1.

Those pressure detectors are known already, the resonant circuit being driven by an oscillator and the inherent frequency thereof, which is normally in the MHz range, fluctuating depending on the changeable capacity so that the frequency fluctuation of the oscillator signals can be converted into a correspondingly fluctuating direct voltage by means of a frequency detector. The frequency detector for such a pressure detector is conventionally made adjustable so that it can be adjusted to the carrier frequency of the detector-oscillator system, for instance, in a manner such as to give no voltage when the detector is not exposed to any pressure. (VDI Report No. 93, "Process of the Electrical Pressure Measuring and Application Thereof", Dusseldorf, 1966, p. 44).

These pressure detectors known already are not adequate for all cases, since their dimensions are too large, they are connected by cables with the other components of the system, and they have no sufficient long-term stability.

There are also known capacitive pressure probes in which a thin, stretched high-quality steel diaphragm is welded with a high-quality steel housing, and that with an insulated electrode not situated under the diaphragm forms a variable capacity. This known pressure probe has electronics with pulse width modulation of a center frequency of about 100 kHz, a digital control converting the pressure-depending capacity changes in a direct voltage signal (Series 237 of Setra Systems Inc.). But the stability of this pressure probe and in particular the temperature dependence are not sufficient for all uses, for many of which the dimensions are far too large, mainly on account of the expensive electronics situated in the immediate proximity of the variable capacity, to obtain the direct-voltage measuring signal, and the required cable connection with the other components of the whole system is likewise inadmissible in a series of cases.

Also known are piezoresistive semiconductor pressure probes that are offered in small dimensions (about 2 mm. diameter and 6 mm. length) (EPI-080 of Entran Devices, Inc.), but these require expensive gauging steps on account of their insufficient stability and temperature dependence (M. Gaaz, "Registration of Intracranial Pressure", University Appointment Paper, Wurzburg 1980, p. 45–56), which make necessary at least periodically a physical connection with other components of the system.

In addition it has also become known already to insert a semiconductor pressure detector in a wireless transmitting probe together with a temperature detector with which to modulate, with the signals of both detectors, a telemetry transmitter situated in the probe and analytically to eliminate the temperature drift of the pressure detector, wherein the probe was wirelessly supplied with energy ("Medical & Biological Engineering & Computing", January, 1979, pages 81–86). But hereby zero drift and calibration of the pressure meter cannot be determined and much less adjusted; in addition, the stabilities of both the transmitter oscillator and the receiver oscillator enter in the measurement, and each one of these deficiencies alone already forbids a long-term measuring even if in the publicity a long operation period has been discussed as possible. Besides, it is common to all known pressure detectors that the production costs are high.

Accordingly, the invention is based on the problem of making available a pressure detector that is small, that requires a small cost of production, that has great stability and independence of temperature, and that can be used without physical connection to the whole system (cable, pressure hose). Those pressure detectors were in general needed where the measuring or pressure space should or must remain movable independently of the whole measuring system, but also where pressure had to be measured in places of difficult access. By way of example herebelow, the measuring of the intracranial pressure is taken as basis; another use is, for example, the checking of air pressure in KFz series. Let it be expressly pointed out that hitherto there has been no pressure meter that could simultaneoulsy fulfill all the established requirements—thus, it has not hitherto been possible, for instance, to achieve long-term stability in telemetry systems on account both of lack of possibility of recalibration and of the inevitable different aging of the two participating oscillators, or to obtain sufficiently small dimensions (diameters of less than 7 mm., since larger holes in the skull bone do not close up again) with the necessary precision at a cost that permits using the detector as an expendable instrument, which is practically necessary in the case of implanted detectors, at least in routine operation, on account of mechanical damages.

Taking as point of departure the pressure detector of the type mentioned at the beginning, the stated problem is solved according to the invention by the steps set forth in the characteristic part of claim 1.

The steps according to claim 2 were taken to reinforce the measuring action; there also results here the advantage that the capacity is simultaneously increased and thus, as it is known in the case of cavity resonators, while the diameter remains the same, the length of the cavity resonator, that is, of the cylindrical cup, can be shortened.

The axial length of the cup can be more, or also additionally, shortened when the step of claim 3 is followed; helicoidal inner conductors for cavity resonators are known as such (for instance, Funkschau 1961, number 10, page 261). A specially good temperature independence and stability are obtained with a development of the invention according to claim 4 and in particular claim 5; ceramic is known to be extensively insensitive to practically all influences in question, specially aging and temperature, and with equal temperature expansion coefficients of spools and cup a possible temperature dependence of the cavity resonator is also eliminated. The electrical conductivity of the materials in question would impair the excellence of the cavity resonator, which is avoided by coating. In this manner there is to be achieved an improvement of the temperature independence by at least the factor 20 in comparison to the already known capacitive pressure detectors, and a long-term stability on the order of $10^{-5}$ and better. As material for the cup there is considered above all, together with ceramic, high-quality steel in an adequate alloy. There has been earlier maintained the opinion that in the pressure detector of the kind mentioned at the beginning a relatively higher wiring expense was needed (VDI report No. 93, loc. cit.). But according to the invention it has been found that the wiring expense for the pressure detector proper can be kept very low since the wiring expense required for the frequency detector can be arranged with oscillator even at great spatial distance from the resonant circuit, and thus sufficiently small dimensions of the pressure detector can be achieved, specially when the pressure detector is developed according to claim 7 and in particular claim 8. With the step according to claim 8, the energy requirement of the oscillator is reduced according to the keying ratio, and thus the current supply therefor can also be reduced, which applies both to a battery (round cell) and to the wireless current supply known per se.

Unlike in the conventional telemetry technique, in the pressure detector according to the invention there is not needed for the wireless transmission of the oscillator signal, any separate transmitter, the supplement according to claim 9 being enough. In the small dimensions sought, the efficiency of an antenna is naturally limited, and thus, precisely in relation to the low power available, the radiated signal is weak so that the transmission is sensitive to disturbance. In the cases where strong disturbances are to be expected, there has been conveniently developed the pressure detector of the invention according to claim 10 wherein the frequency divider is needed in order to serve the purpose with a luminous diode of low sampling frequency.

A certain difficulty is constituted by the mounting of the pressure detector, specially in the skull bone. For this purpose there is known an adapter sleeve according to the preamble of claim 11 that has an outer thread wherewith it is screwed on with simultaneous cutting of the thread into the wall, specially, therefore, the skull bone. In this adapter sleeve the pressure detector proper is then in turn screwed on (Gaab, loc. cit., FIG. 13, partial illustration, p. 9). Such an adapter sleeve has mainly two disadvantages: after long use the thread can grow in so that at the end of the test the adapter sleeve can only be removed with difficulty, and when screwed on the adapter sleeve twists easily so that the diaphragm of the pressure detector inserted is no longer parallel with the wall inner surface, which in any case can lead to considerable measuring errors when measuring intracranial pressure. To achieve a perfect position of the adapter sleeve and avoid the danger of twisting, this known adapter sleeve has been modified according to the invention, as indicated in the characteristic part of claim 11. The portion of the spring cage that extends into the pressure space forms a bead that when the adapter sleeve is inserted projects over the inner edge of the bore and thus rectifies misalignments of the sleeve with the wall bore until the sleeve shoulder perfectly supports itself on the bore shoulder and for this purpose must project from the outer surface of the spring cage forming a relatively abrupt angle. In the last part of the insertion path, the ribs give a certain guidance, but mainly, when the adapter sleeve is withdrawn, they take care that the individual spring tongues be gradually pressed inwardly so that the external periphery is reduced and a relatively abruptly projecting bead is also brought to a sufficiently small outer diameter in order to be outwardly drawn without obstacle through the narrow bore.

When the wall material is comparatively soft, which is substantially the case with the skull bone, the guiding of the adapter sleeve when inserted and the precise axial alignment thereof by support on the bore shoulder can be considerably improved by following the steps of claim 12.

The invention is explained in further detail with reference to the drawing; wherein.

Figure 1:
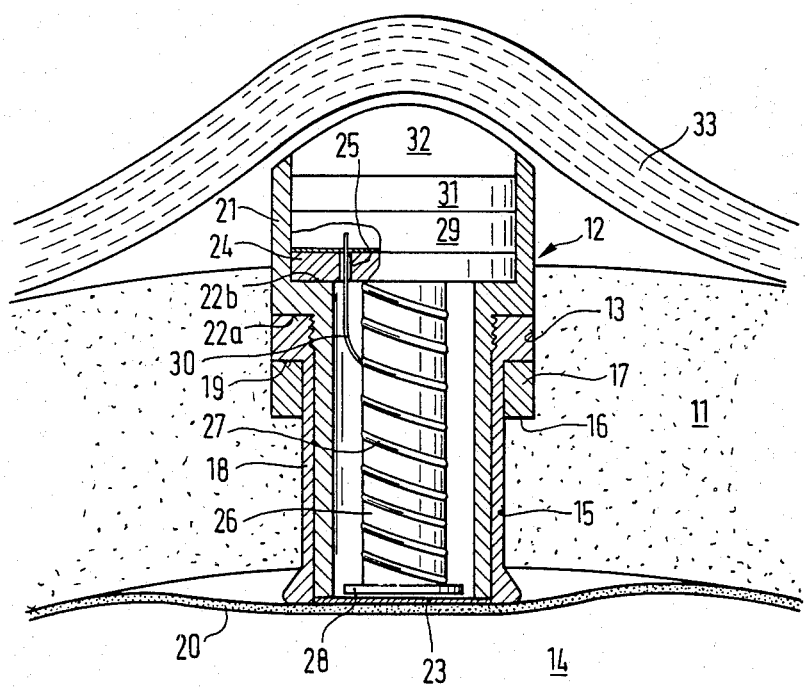
FIG. 1 is a section through a pressure detector implanted in a skull bone.

According to FIG. 1 there is provided in a skull bone 11 a graduated borehole 12 that has a wider portion 13 shown at the top in FIG. 1 and facing the skull interior 14 a narrower portion 15, said portions being interconnected by a radially extending shoulder 16. The length of the narrow borehole portion 15 is fixedly predetermined, which is ensured in a manner known per se by using a self-uncoupling miniborer. On the shoulder 16 rests an intermediate ring 17 having an inner diameter equal to the diameter of the narrower borehole portion 15 and an outer diameter equal to the diameter of the wider borehole portion 13 and consisting of an inert material such as high-quality steel.

In the bore and the intermediate ring 17 is inserted an adapter sleeve 18 that sits on the intermediate ring 17 with a radial shoulder 19 and through the intermediate ring 17 and the narrow bore portion 15 extends to a fixedly predetermined extent into the space between the skull bone 11 and the duramater 20 that surrounds the brain. The adapter sleeve 18 will be later explained in more detail with reference to FIGS. 2 and 3.

In the adapter sleeve is in turn inserted a pressure detector according to the invention, which in the illustrated embodiment is screwed on but other kinds of fastening means such as a bayonet assembly can be considered. This fastening is conveniently limited to the area above the radial shoulders 19 of the adapter sleeve 18 in order to keep the thin-walled portion of the sleeve 18 free of corresponding stresses.

The pressure detector proper has a housing in the form of a graduated cylindrical pipe that in the interior is of good electric conductivity; the pipe preferably consists of high-quality steel and in the interior is coated with silver. The outer diameter of the wider portion of the housing 21 corresponds to the diameter of the wider bore portion 13, the remaining part of the housing 21 being adapted to the interior of the adapter sleeve 18; the shoulder 22a formed by the housing step sits at the top on the adapter sleeve 18 and the end of the housing that faces the duramater 20 terminates with the end of the adapter sleeve 18 likewise facing the duramater 20. Said end of the housing 21 facing the duramater 20 is sealed with a diaphragm 23 that is elastically yieldable in a manner known per se and has good electric conductivity at least in the interior. It can be integrally made with the housing 21 or it can be separately mounted thereon in which latter case copper beryllium is specially considered as material. On the inner shoulder 22b of the housing 21 corresponding to the outer shoulder 22a, there is situated a false bottom 24 that in its interior is of good electric conductivity and has an opening 25. In the cylindrical container or cup defined by the interior of the housing 21 and the false bottom 24 there is coaxially situated a ceramic spool 26 that carries a burnt-up silver winding 27 and an electrically conductive coating or plate 28 on the end thereof that is shown at the bottom in the drawing. The silver winding 27 is connected with good electric conductivity both with the coating or plate 28 and with the electrically conductive false bottom 24. The thermal expansion coefficients of housing 21 and spool 26 are equal in the preferred embodiment.

On the side of the false or cut bottom 24 remote from the ceramic insulating member 26 is situated an oscillator 29, an FET circuit in the illustrated embodiment, that is electrically connected by a line 30 with a point of the silver winding 27 in the manner of a Franklin oscillator 80 as to maintain low the influence of the oscillator on the resonance circuit (cavity resonator) formed by the winding 27 and the capacity between plate 28 and diaphragm 23 so that the effect of aging of the oscillator can be practically disregarded even after a very long period of time (several months or even years). Instead of this galvanic coupling by a line 30 there can also be provided an inductive coupling known per se in cavity resonators or another coupling that only slightly stresses the resonance circuit.

Upon the oscillator 29 is situated a current supply 31. When the measuring duration is relatively short (a few days) a battery in the form of a round cell can be provided as current supply 31; but if a longer measuring duration is to be expected, there is conveniently used a wireless current supply known per se that essentially comprises a receiving antenna and a rectifier.

Upon the current supply 31 is an antenna 32 connected with the oscillator 29 with which antenna the oscillator signal is radiated through the whole covering film 33.

In a variant it is possible to use, instead of the antenna 32 diagrammatically shown as a coil antenna, a silicon hose that leads outwardly through the film 33. While in the illustrated embodiment of the pressure detector the interior of the housing 21 is under known pressure, specially a defined underpressure (vacuum), the housing interior could, in the case of such hose connection, be under the air pressure prevailing at the moment so that the pressure detector emits a signal corresponding to the difference between the intracranial pressure and the air pressure instead of a signal corresponding to the absolute intracranial pressure like in the illustrated embodiment.

In another embodiment that is practically identical in mechanical construction, an infrared-emitting luminous diode is provided instead of an antenna 32; in this case care must be taken that the filling compound used be infrared permeable. There is further conveniently inserted a frequency divider wiring between the luminous diode and the oscillator 29, it being thus possible to use luminous diodes having a switch frequency below the basic frequency of the resonance circuit mentioned.

The pressure detector works as follows: Changes of pressure in the space 14 are relayed through the elastic duramater 20 to the elastic diaphragm 23 so that their distance from the plate 28 and thus the capacity between these parts is a criterion for the pressure space 14. This capacity determines, together with the inductivity of the winding 27, the frequency of the resonator cavity formed by those parts together with the housing 21 and the false bottom 24 so that the connected oscillator 29 swings to this frequency. The oscillator vibration is radiated as oscillator signal from the antenna 32 and in a manner known per se can be absorbed by a separate receiver to which is connected a frequency meter or the like the output signal of which thus constitutes a criterion for the pressure in space 14.

Figure 2:
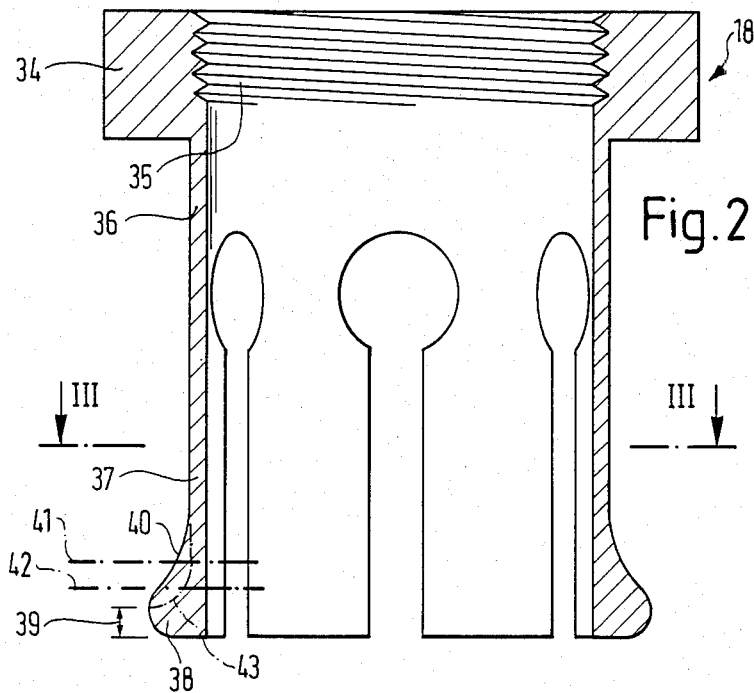
FIG. 2 is a longitudinal section through an adapter sleeve for mounting a pressure detector.
Figure 3:
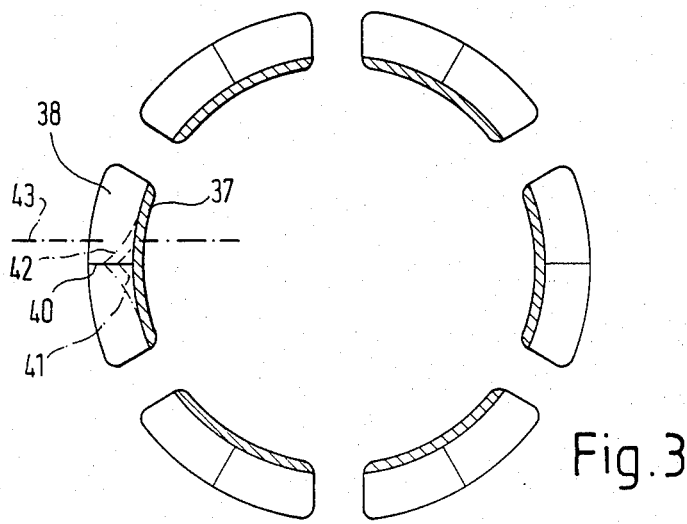
FIG. 3 is a section along line III—III in FIG. 2.

The adapter sleeve 18 is illustrated in more detail in FIGS. 2 and 3. It has a ring 34 in the area of which is provided an inner thread 35, which in other embodiments can be replaced, as it has been said, by other fastening means, and a tubular portion 36 that is split up into a number, six in the illustrated embodiment, of spring tongues 37 so as to form a spring cage. The outer diameter of the spring cage is adapted to the inner diameter of the narrow bore portion 15 with the exception of the portion that overhangs the inner boundary of the bore 12 (FIG. 1), which has a larger outer diameter so as to form an outer bead or an outwardly projecting flange 38 the axial dimension 39 of which is the extent to which the bead projects over the inner surface of the skull bone (FIG. 1).

In addition each spring tongue 37 has a sharp-edged rib 40 which runs from the outer periphery of the bean 38 to the outer surface of the accessory spring tongue 37 on a site that is within the narrow bore portion 15 (FIG. 1); in the illustrated embodiment the rib 40 extends into the bore further than the bean 38 projects over the outer periphery of the spring cage. The sharp-edged rib 40 gradually passes over from the sharp edge into the outer surface of the spring cage, there being shown in dotted lines in FIG. 3, in a spring tongue, two sections that mark the outer contour in two cross sections 41, 42 indicated in FIG. 2. The outer bead contour resulting therefrom is indicated in FIG. 2 as dotted line 43 corresponding to the intersection line 43 marked in FIG. 3.

By means of this adapter sleeve a pressure detector is inserted in a manner such that after producing, as known per se, the graduated bore 12, the intermediate ring 17 together with the adapter sleeve 18 are inserted, the bead being clamped in the inner space of the intermediate ring 17 so as to be compressed on the inner diameter of the narrow bore portion 15. As soon as the intermediate ring 17 abuts on the bore shoulder 16, the adapter sleeve 18 is pushed forward, which is easily done, since the outer periphery of the bead 38 is also compressed to the dimension of the narrow bore portion 15, and therefore can pass without difficulty. As soon as the bead, as shown in FIG. 1, emerges from the bore 12, 15 at the lower end, the individual spring tongues can give way outwardly so that the outer bead 38 can expand beyond the underside of the skull bone 11. Eventual irregularities in the inner surface are here compensated by the diagonally extending ribs 40 that take care of a certain axial force with which the ring 34 of the adapter sleeve 18 is drawn to the intermediate ring 17 so that the adapter sleeve 18 assumes the desired position. The ribs 40 at the same time compress themselves into the bone 11 that is relatively soft compared to the ribs. The pressure detector is then inserted, that is, screwed on in the illustrated embodiment, and if the individual spring tongues still have not achieved by then full expansion, they are outwardly pressed to full expansion by the pressure detector. In removing the pressure detector, the operation is reversed, that is, the pressure detector is first removed (unscrewed), which is easily possible since the adapter sleeve 18 cannot rotate along on account of the ribs 40, and the adapter sleeve 18 is withdrawn for which a drawing tool can be screwed on instead of the pressure detector, at the same time the outer bead 38 carried along the intermediate ring 17. By virtue of the ribs 40, which for this purpose pass over in the illustrated manner into the outer surface of the respective spring tongue forming a relatively small angle, the spring tongues 37 are inwardly compressed as soon as even an insignificant portion of the adapter sleeve 18 has been outwardly drawn; due to the wedging action related thereto there also results a sufficient force that in any case releases the spring tongues from the bone even if there have been unavoidable pastings. As long as the diameter of the wide portion 13 of the bore 12 is not larger than about 7 mm, the hole 12 closes up again after removal of the detector and adapter sleeve 18. Since the diameter of the pressure detector according to the invention can be kept at less than 5 mm, the largest diameter of the adapter sleeve 18 can also be kept small enough to permit a closing up of the bore 12.

We claim:

1. A pressure detector, for measuring the intracranial pressure, including a sensor housing which comprises a cavity resonator circuit of a specific inductance and a capacity changeable in dependence on the pressure and an oscillator connected with said resonator circuit, said resonator cavity circuit comprising a cylindrical cup of electrically conductive material, an elastically yieldable, electrically conductive diaphragm that seals its front surface, and a helical inner conductor ending in a flat electrode and situated coaxially in said cup spaced from said diaphragm and secured to the bottom of said cup, wherein the cavity resonator circuit is a resonator with a helical inner conductor, said helical inner conductor being built upon a ceramic body situated coaxially in the said cup, said helical inner conductor being provided on its front face with the said flat electrode, and further characterized in that the said oscillator for the cavity resonator circuit is situated inside of the sensor housing.

2. A pressure detector according to claim 1, characterized in that the end of said inner conductor opposite said diaphragm has a larger diameter than the remaining part of said inner conductor and is situated parallel with said diaphragm.

3. A pressure detector according to claim 1, characterized in that said inner conductor is disposed in the form of a spiral the axis of which is the axis of said cup.

4. A pressure detector according to claim 3, characterized in that said inner conductor is a silver coating burnt up on a ceramic spool.

5. A pressure detector according to claim 4, characterized in that said resonator cavity cup consists of a material having the same temperature expansion coefficient as the ceramic of said spool and said inner surface of said resonator cavity cup is coated with a material of good electric conductivity, specially silver.

6. A pressure detector according to claim 5, characterized in that the material of said resonator cavity cup is high-quality steel.

7. A pressure detector according to claim 1, characterized in that said oscillator is situated on the side of said cup bottom remote from said inner conductor.

8. A pressure detector according to claim 1, characterized in that a wiring is provided for clocking said oscillator.

9. A pressure detector according to claim 1, characterized in that an antenna is connected to said oscillator for wireless disengagement of said oscillator signal.

10. A pressure detector according to claim 1, characterized in that a frequency divider is connected to said oscillator and an infrared-emitting luminous diode is connected to said frequency divider.

11. An adapter sleeve for mounting a pressure detector in a graduated bore by means of a wall that surrounds the space whose inner pressure must be determined, wherein the narrowest part of said bore faces the pressure space and the spacing between the inner surface of said wall and the shoulder between said narrowest part of said bore and the remaining part is firmly predetermined and said adapter sleeve has a shoulder that supports itself on the bore shoulder and extends up to a firmly predetermined extent into the pressure space, characterized in that the portion of said adapter sleeve between said sleeve shoulder and the end facing said pressure space is made as a spring cage, the outer diameter of the portion of said spring cage that extends into said pressure space being larger than the inner diameter of the narrowest part of the step bore, and each spring tongue of said spring cage has a sharp-edged rib stretching from the outer periphery of the portion of said spring cage that extends into said pressure space to a point lying securely within the narrowest wall bore portion.

12. An adapter sleeve according to claim 11, characterized in that an intermediate ring is situated between said bore shoulder and said sleeve shoulder.

* * * * *